United States Patent
Fisher et al.

(10) Patent No.: US 7,892,777 B2
(45) Date of Patent: Feb. 22, 2011

(54) METHODS FOR MEASURING WHETHER A TREATMENT AFFECTS RPTP-κ ACTIVITY

(75) Inventors: Gary J. Fisher, Ann Arbor, MI (US); Yiru Xu, Ann Arbor, MI (US); John J. Voorhees, Ann Arbor, MI (US)

(73) Assignee: The Regents Of The University Of Michigan, Ann Arbor, MI (US)

( * ) Notice: Subject to any disclaimer, the term of this patent is extended or adjusted under 35 U.S.C. 154(b) by 201 days.

(21) Appl. No.: 12/218,532

(22) Filed: Jul. 16, 2008

(65) Prior Publication Data

US 2009/0022677 A1 Jan. 22, 2009

Related U.S. Application Data

(60) Provisional application No. 60/959,823, filed on Jul. 17, 2007.

(51) Int. Cl.
*C12Q 1/42* (2006.01)
(52) U.S. Cl. .......................................... 435/21; 424/59
(58) Field of Classification Search .................. 435/21; 424/59
See application file for complete search history.

(56) References Cited

U.S. PATENT DOCUMENTS 5,856,162 A * 1/1999 Schlessinger et al. ....... 435/196
5,863,755 A * 1/1999 Schlessinger et al. ...... 435/69.1
2005/0037380 A1 * 2/2005 Schlessinger et al. .......... 435/6

FOREIGN PATENT DOCUMENTS

WO    WO 02/20846    * 3/2002

OTHER PUBLICATIONS

Xu, Y. et al. Oxidative Inhibition of Recpetor Type Protein Tyrosine Phosphatase kappa by UV Irradiation . . . J of Biological Chemistry 281(37)27389-97, Sep. 15, 2006.*
Xu, Y. et al. Receptor Type Protein Tyrosine Phosphatase kappa Regulates EGF Receptor Function. J of Biological Chemistry 280(52)42694-700, Dec. 30, 2005.*

* cited by examiner

*Primary Examiner*—Ralph Gitomer

(57) ABSTRACT

Methods are provided for ascertaining and measuring RPTP-κ activity in response to insults such as UV irradiation and with respect to administration of a treatment and/or composition. Attenuation of EGFR activity by RPTP-κ affects aspects of photoaging, including damage to the skin, suppression of the immune system, DNA damage, and connective tissue degradation. Intervention with respect to the effects of photoaging can include protection of RPTP-κ from oxidation. The methods can be used for discovery of anti-aging treatments, adjuncts, or other preventative treatments, such as sunscreens.

10 Claims, 15 Drawing Sheets

METHODS FOR MEASURING WHETHER A TREATMENT AFFECTS RPTP-κ ACTIVITY

CROSS-REFERENCE TO RELATED APPLICATIONS

This application claims the benefit of U.S. Provisional Application No. 60/959,823, filed on Jul. 17, 2007. The disclosure of the above application is incorporated herein by reference.

FIELD

The present disclosure generally relates to methods for measuring effects of ultraviolet irradiation on cellular systems linked to photoaging, including the activity of receptor protein-tyrosine phosphatase kappa.

INTRODUCTION

The statements in this section merely provide background information related to the present disclosure and may not constitute prior art.

The skin is the largest organ in the human body and is the only organ that is directly and continuously exposed to the environment. Acute exposure to the sun, due to solar ultraviolet (UV) radiation, can cause various types of damage to the skin, including sunburn (erythema), suppression of the immune system, DNA damage, and connective tissue degradation. Approximately one million people in the USA develop skin cancer each year. Almost every person on earth experiences some degree of photoaging—the ageing of skin due to repeated exposure of the skin to solar UV radiation. As distinguished from intrinsic aging or chronoaging (chronological aging) of skin, the epidermis of photoaged skin may be thickened, pigment changes are more frequent, and deep wrinkling may be present. In photoaged skin, the dermal matrix, consisting mainly of collagen and elastic fibers, is degraded over time by the cycle of UV-enhanced breakdown of collagen and elastin.

UV irradiation has been shown to increase matrix metalloproteinases (MMPs) above normally occurring levels in human skin. MMPs are a family of enzymes that degrade collagen and elastin, which are structural proteins important to the integrity of the dermal matrix. MMPs induced by UV irradiation exposure are upregulated via cytokine receptor and growth factor receptor pathways. The increase in MMPs after UV exposure through the growth factor receptor pathways includes activation of the epidermal growth factor receptor (EGFR, or ErbB).

The epidermal growth factor receptor (EGFR) is a ubiquitously-expressed, cell surface, transmembrane receptor that possesses intrinsic protein tyrosine kinase activity. Functional activation of EGFR results from increased phosphorylation of specific tyrosine residues in its C-terminal cytoplasmic domain. Phosphotyrosine residues function as binding sites for the assembly of protein complexes that initiate signaling pathways that, down-stream, regulate cellular function. EGFR is highly expressed in human skin cells (keratinocytes) in vivo and in vitro. Emerging evidence indicates that EGFR is a critical functional mediator of cellular responses to a diverse array of extracellular stimuli, including ligands for other cell surface receptors.

UV irradiation rapidly increases EGFR tyrosine phosphorylation in human keratinocytes in vivo and in culture. This EGFR activation induces certain signaling pathways (termed the mammalian UV response) that include mitogen-activated protein kinases (MAP kinases), phosphatidylinositol 3-kinase/Akt (PI-3 kinase/Akt), and phospholipase C/protein kinase C (PLC/PKC). These signaling pathways induce a variety of transcription factors and their target genes, including AP-1 and matrix metalloproteinases (MMPs), respectively, which play critical roles in the development of skin cancer and photoaging. Accordingly, EGFR tyrosine phosphorylation is important in the pathophysiology of UV irradiation induced human skin damage. In addition, EGFR activation protects against UV irradiation induced apoptosis through the activation of the PI-3-kinase/AKT pathway.

Importantly, the EGFR can self-activate, via its intrinsic enzymatic activity for self-phosphorylation (intrinsic tyrosine kinase activity). Binding of the EGFR to an extracellular ligand can increase the level of phosphorylation of its intracellular (cytoplasmic) domain, thereby resulting in autoactivation. Intrinsic tyrosine kinase activity causes of activation of EGFR without ligand binding. Once activated, an EGFR can activate other EGFRs in the membrane, forming a cascade, an amplified signal to increase production of AP-1 and MMPs.

Receptors with intrinsic kinase activity are the subject of much research in cancer physiology because if unregulated they result in uncontrolled cell growth, a hallmark of cancer. Various compounds have been discovered and invented to inhibit EGFR activation, by interfering with ligand or ATP binding. The body's own system for keeping the EGFR intrinsic kinase activity under control is complex and, as demonstrated by the present disclosure, involves dephosphorylation by receptor type protein-tyrosine phosphatase kappa (RPTP-κ).

SUMMARY

The present disclosure is drawn to methods involving receptor type protein-tyrosine phosphatase kappa (RPTP-κ). Oxidative inhibition of RPTP-κ by UV irradiation activates EGFR. In some embodiments, a method for measuring UV irradiation based inhibition of RPTP-κ activity includes irradiating RPTP-κ with UV and measuring the activity of RPTP-κ. Methods may use intact cells containing RPTP-κ and visible light or sunlight may be used as an irradiation source. Inhibition of RPTP-κ may also be measured in the presence of a source of reactive oxygen species. Measuring the activity of RPTP-κ may include measuring the oxidative state of RPTP-κ, where an increase in the ratio of oxidized RPTP-κ to total RPTP-κ following UV irradiation is indicative of UV-based inhibition. Measuring the activity of RPTP-κ may also include measuring phosphatase activity of RPTP-κ, wherein a decrease in phosphatase activity is indicative of UV-based inhibition.

In some embodiments, a method is provided for measuring whether a treatment affects UV irradiation based oxidation of RPTP-κ in a cell. The treatment is applied to at least one cell expressing RPTP-κ. Treated and untreated cells are exposed to UV irradiation and the activity of RPTP-κ is measured. A difference in the activity of RPTP-κ following UV irradiation in the treated and untreated cells is indicative of the treatment affecting RPTP-κ activity. The treatment may be identified as protecting RPTP-κ activity when the ratio of oxidized RPTP-κ to total RPTP-κ following UV irradiation is less in the treated cell compared to the untreated cell or when the phosphatase activity of RPTP-κ is greater in the treated cell compared to the untreated cell. These methods may also be used to measure whether a treatment affects oxidation of RPTP-κ by a reactive oxygen species in lieu of UV irradiation or in addition to UV irradiation.

In some embodiments, a method is provided for attenuating activity of epidermal growth factor receptor (EGFR) following UV irradiation of a cell, the cell expressing EGFR and RPTP-κ. The method includes inhibiting the oxidation of RPTP-κ. Inhibiting the oxidation of RPTP-κ may include treating the cell with *Laminaria japonica* extract. The method may also include measuring the inhibition of RPTP-κ oxidation.

In some embodiments, the present disclosure provides methods for determining whether an insult affects RPTP-κ activity. Cells expressing RPTP-κ are provided and initial RPTP-κ activity is measured. The cells are exposed to the insult and RPTP-κ activity is measured. The insult is identified as affecting RPTP-κ activity if the RPTP-κ activity measured after exposure to the insult is different than the RPTP-κ activity prior to the insult. The cells may further express EGFR and EGFR phosphorylation may be measured before and after exposure to the insult. The insult may also be identified as inhibiting RPTP-κ activity if RPTP-κ activity measured after exposure to the insult is decreased relative to initial RPTP-κ activity prior to the insult and EGFR phosphorylation is increased relative to initial EGFR phosphorylation.

In some embodiments, the present disclosure includes methods for determining whether a composition protects RPTP-κ activity from an insult that increases EGFR phosphorylation. The methods include administering the composition to a cell having a known RPTP-κ activity. The cell is then exposed to the insult and the activity of the RPTP-κ in the cell after exposure to the insult is measured. The composition is identified as protecting RPTP-κ activity if the measured activity of the RPTP-κ in the cell after exposure to the insult is about the same as the known RPTP-κ activity.

The present disclosure further provides methods for selecting treatments, including compositions, for topical administration that include determining whether a candidate compound protects RPTP-κ in human skin cells by measuring the level of EGFR phosphorylation in the presence of a reactive oxygen species (ROS) following treatment and/or administration of the composition. The treatment and/or composition are rejected if the level of EGFR phosphorylation is greater than a predetermined level. In another embodiment, a method for determining the ability of a composition to protect RPTP-κ against oxidative degradation includes measuring the level of EGFR phosphorylation in a mixture of the candidate compound and an EGFR agonist.

In some embodiments, the present disclosure includes compositions that treat photoaging by protecting RPTP-κ activity. Such a composition includes an alcohol extract of *Laminaria japonica*. The extract may be suspended in a vehicle suitable for topical administration to the skin. The alcohol may be methanol and/or the alcohol extract may be dried. Dried *Laminaria japonica* extract may be suspended in an aqueous or organic vehicle or may be suspended in a vehicle suitable for topical administration. Vehicles suitable for topical administration include lotions, creams, and ointments. These vehicles may be further formulated with other ingredients into sunscreens, for example.

The present disclosure provides several benefits and advantages relating to understanding, measurement, and intervention with respect to UV irradiation based photoaging. UV irradiation rapidly increases tyrosine phosphorylation of EGFR (i.e., activates EGFR) in human skin. EGFR-dependent signaling pathways drive increased expression of matrix metalloproteinases, whose actions fragment collagen fibers, the primary structural protein component in skin connective tissue. Connective tissue fragmentation, which results from chronic exposure to solar UV irradiation, is a major determinant of premature skin aging (photoaging). UV irradiation generates reactive oxygen species, which readily react with conserved cysteine residues in the active site of protein-tyrosine phosphatases (PTP). EGFR activation by UV irradiation results from oxidative inhibition of receptor type protein-tyrosine phosphatase kappa (RPTP-κ). RPTP-κ directly counters intrinsic EGFR tyrosine kinase activity (i.e., phosphorylated EGFR), thereby maintaining EGFR in an inactive state. Reversible, oxidative inactivation of RPTP-κ activity by UV irradiation shifts the kinase-phosphatase balance in favor of EGFR activation. The present disclosure delineates a novel mechanism of EGFR regulation and identifies RPTP-κ as a key molecular target for antioxidant protection against skin aging.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The present disclosure will become more fully understood from the detailed description and the accompanying drawings, wherein:

FIG. 1A is a histogram of RPTP-κ activity as a function of hydrogen peroxide concentration; FIG. 1B is a histogram of EGFR tyrosine phosphorylation as a function of hydrogen peroxide concentration with and without ATP; and FIG. 1C is a histogram of EGFR tyrosine phosphorylation in the presence of RPTP-κ and/or hydrogen peroxide, and a Western blot of tyrosine phosphorylated EGFR under the conditions graphed;

FIG. 3A is a histogram of EGFR tyrosine phosphorylation in the presence of EGF or UV irradiation, with and without an antibody that blocks ligand binding to EGFR; FIG. 3B is the change in RPTP-κ protein versus time upon UV exposure, and a Western blot showing the same; FIG. 3C is a histogram showing RPTP-κ activity before and after UV irradiation; FIG. 3D is a histogram of RPTP-κ activity before and after UV irradiation, with irreversible oxidation of RPTP-κ and in the presence or absence of an agent to reduce oxidized RPTP-κ; and FIG. 3E is a histogram of RPTP-κ oxidation before and after UV irradiation exposure;

FIG. 6A is a color photo depicting in situ antisense probe hybridization for RPTP-κ mRNA (with sense probe as control); FIG. 6B is a color photo showing RPTP-κ protein expression detected by immunohistochemistry; FIG. 6C is a color photo depicting co-localization (yellow) of EGFR (green) and RPTP-κ (red) proteins; and FIGS. 6D and 6E depict RPTP-κ protein and RPTP-κ activity before and after UV irradiation exposure, respectively;

Figure 1A:
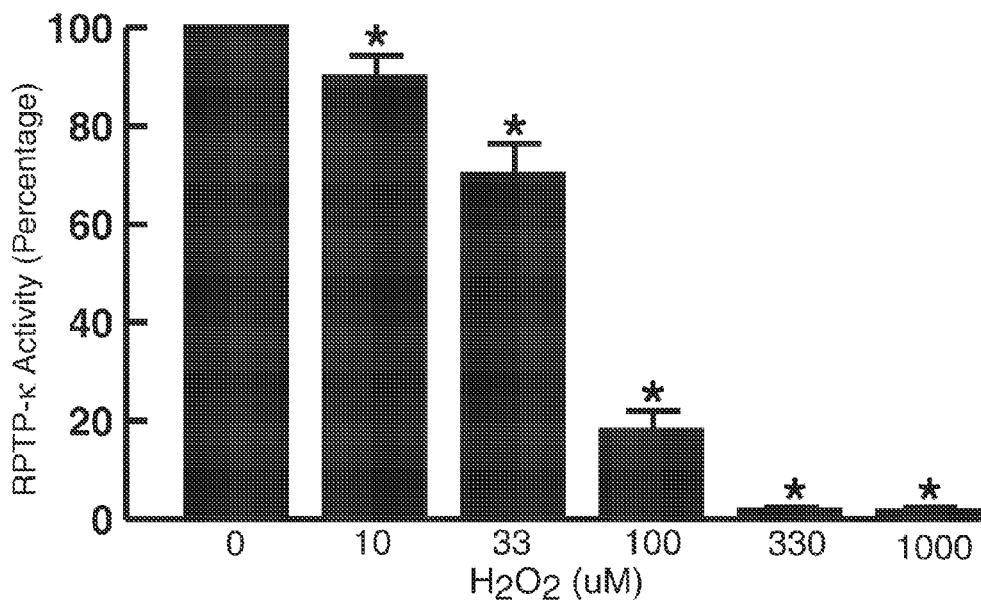
FIGS. 1A-C depict in vitro experimental results.

The results depicted in FIGS. 1-6 are published by Xu, Y., et al., in *J. Biol. Chem.*, 15 Sep. 2006, 281 (37): 27389-97; the disclosure of which is incorporated herein by reference.

DETAILED DESCRIPTION

The following description is merely exemplary in nature of the subject matter, manufacture, and use of one or more inventions, and is not intended to limit the scope, application, or uses of any specific invention claimed in this application or in such other applications as may be filed claiming priority to this application, or patents issuing therefrom.

The present disclosure relates to methods involving EGFR signal transduction as it relates to photoaging. UV-based inhibition of receptor type protein-tyrosine phosphatase kappa (RPTP-κ) activity can increase EGFR activity. Preventing the oxidation of RPTP-κ can attenuate the EGFR signal cascade.

The biological effects of UV irradiation occur as a consequence of absorption of electromagnetic energy by certain molecules within all cells. Excess energy is dissipated either by chemical modification of the absorbing molecule and/or transfer of some portion energy to an acceptor molecule. Molecular oxygen, which is present in high concentrations in eukaryotic cells, can readily accept energy from UV-irradiation absorbing molecules. This photochemical activation of molecular oxygen generates reactive oxygen species (ROS), which can oxidize cellular constituents including proteins, lipids, and nucleic acids.

Members of the protein-tyrosine phosphatase (PTP) family contain an active site cysteine residue that is required for phosphohydrolase activity. This active site cysteine is highly susceptible to oxidation, particularly by hydrogen peroxide ($H_2O_2$). The pKa of the cysteine within the active site is relatively low (5.5) at physiological pH, which promotes formation of the reactive thiolate form. The thiolate reacts readily with $H_2O_2$ to form a stable sulfenic acid, or sulfenylamide species, which renders the phosphatase catalytically inactive. The reversible oxidative inactivation of PTP activity can occur as a consequence of ROS generated in response to growth factor and cytokine receptor activation, and regulates tyrosine phosphorylation-dependent signal transduction pathways.

Oxidative inhibition of PTP activity by ROS may be a mechanism for activation of EGFR by UV irradiation. Investigation of this mechanism is hindered by lack of knowledge regarding phosphatases that directly regulate EGFR at the cell surface. Receptor-type protein-tyrosine phosphatase kappa (RPTP-κ) as a regulator of EGFR tyrosine phosphorylation, in human keratinocytes. RPTP-κ directly dephosphorylates EGFR in vitro, and functions in cells to maintain low levels of EGFR tyrosine phosphorylation in the absence of ligand. RPTP-κ counteracts EGFR intrinsic tyrosine kinase activity by preferentially dephosphorylating EGFR tyrosine residues #1068 and #1173. The present disclosure demonstrates that activation of EGFR by UV irradiation is mediated by oxidative inhibition of RPTP-κ activity.

To illustrate the role of RPTP-κ in UV irradiation regulation of EGFR tyrosine phosphorylation, effects of reactive oxygen species (ROS) on purified RPTP-κ activity and EGFR tyrosine phosphorylation in vitro are examined.

With reference to FIG. 1, oxidative inhibition of RPTP-κ activity is shown to enhance EGFR tyrosine phosphorylation in vitro. Shown in panel A, purified RPTP-κ glutathione S-transferase fusion protein was incubated with the indicated concentrations of $H_2O_2$ at room temperature for 30 min. RPTP-κ activity was measured using phospho-EGFR peptide as substrate. *, p<0.05 versus control. Shown in panel B, purified EGFR, supplemented with EGF and ATP/$Mg^{2+}$, was incubated with the indicated concentrations of $H_2O_2$ at room temperature for 30 min. Samples were subjected to Western analysis for EGFR tyrosine phosphorylation. Levels of phosphorylated EGFR were quantified by chemifluorescent detection. Shown in panel C, purified EGFR, supplemented with EGF and ATP/$Mg^{2+}$, and purified RPTP-κ glutathione S-transferase fusion protein were incubated together in the presence or absence $H_2O_2$ (100 µM), at room temperature for 30 min. Tyrosine phosphorylation of EGFR was quantified by chemifluorescence, as described for panel B. Results are mean±S.E. for three independent experiments. *, p<0.05 versus $H_2O_2$-treated.

Figure 1B:
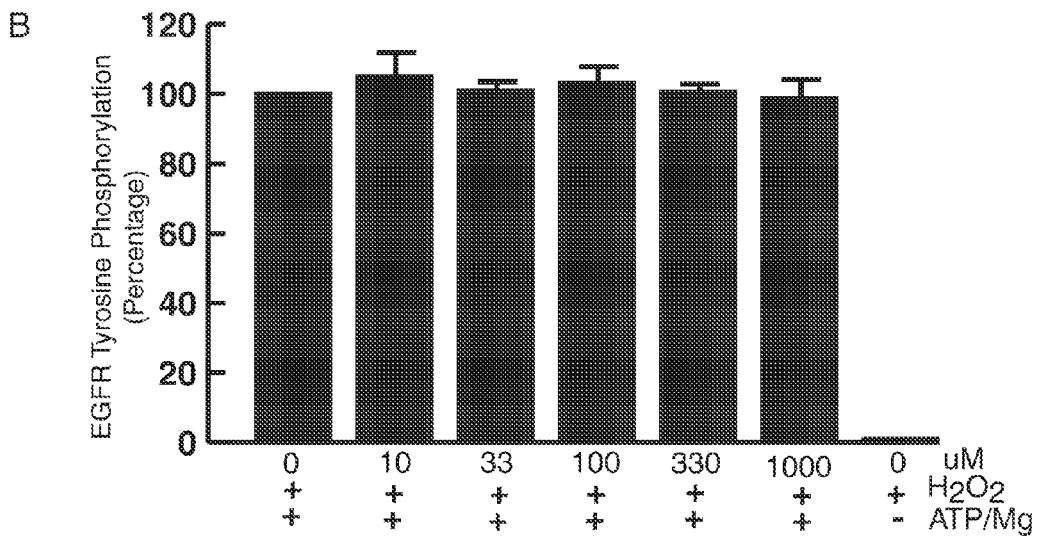
Figure 1C:
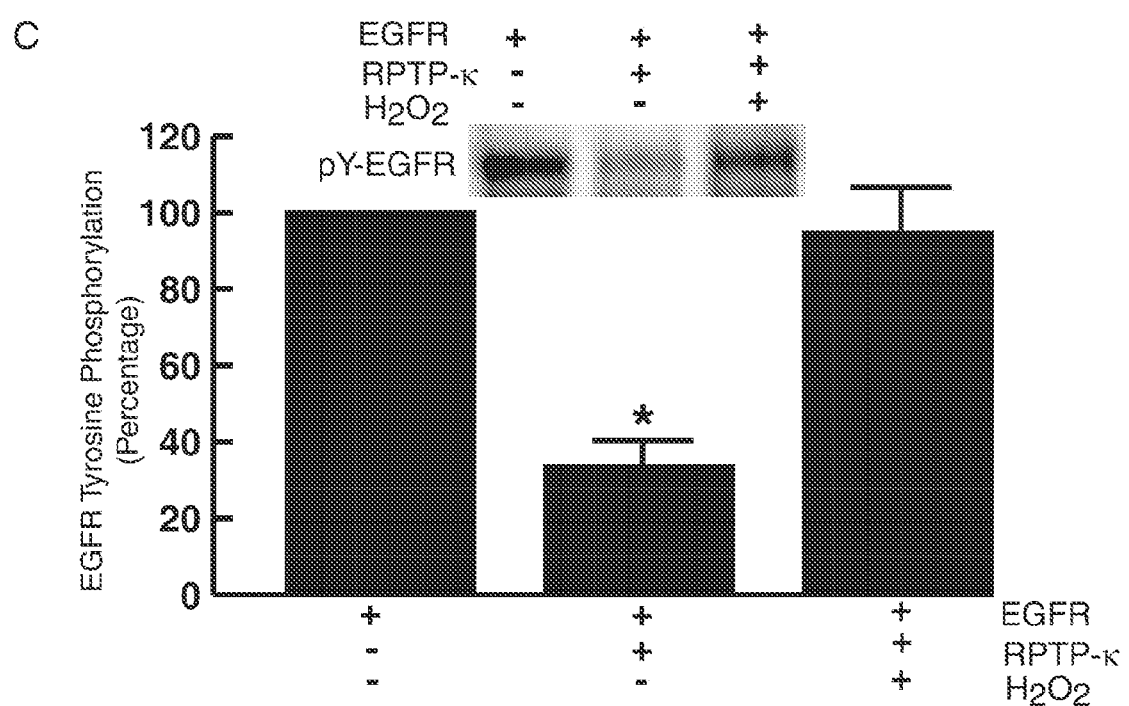

Addition of hydrogen peroxide ($H_2O_2$) caused dose-dependent inhibition of RPTP-κ activity, with 80% loss of activity observed at 100 µM (FIG. 1A). In the presence of ATP/$Mg^{2+}$, purified EGFR was phosphorylated by its intrinsic tyrosine kinase activity. In contrast to RPTP-κ, $H_2O_2$ had no direct effect on tyrosine phosphorylation of purified EGFR, in vitro (FIG. 1B). Incubation of purified RPTP-κ and EGFR together resulted in a low level of steady state EGFR tyrosine phosphorylation, representing the balance between the rates of tyrosine kinase and tyrosine phosphatase activities. In the presence of $H_2O_2$, which inhibits RPTP-κ, EGFR tyrosine phosphorylation increased to the level observed in the absence of RPTP-κ (FIG. 1C). These data provide proof of concept for RPTP-κ dependent regulation of EGFR tyrosine phosphorylation by ROS, in a cell-free system. As used herein, "inhibit" generally means a statistically significant reduction from normal levels as opposed to complete elimination.

To further illustrate effects of UV irradiation on the regulation of EGFR tyrosine phosphorylation by RPTP-κ, a model mammalian cell system is used. Chinese hamster ovary (CHO) cells do not express either EGFR or RPTP-κ.

Figure 2:
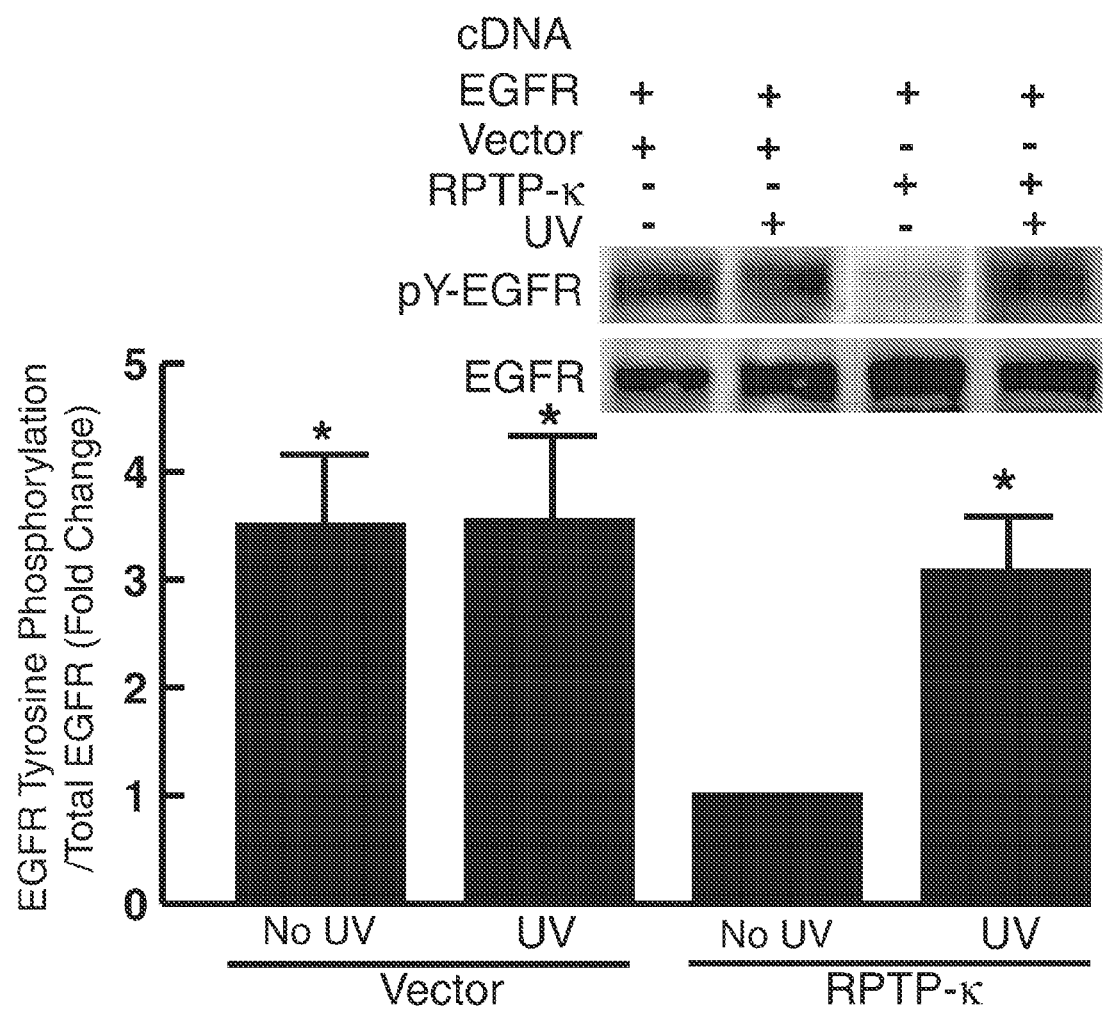
FIG. 2 depicts in vitro experimental results showing a histogram of the fold change in EGFR tyrosine phosphorylation upon UV irradiation with and without RPTP-κ present, and a Western blot of EGFR and tyrosine phosphorylated EGFR.

With reference to FIG. 2, RPTP-κ is shown to reduce constitutive EGFR tyrosine phosphorylation and confer UV induction of EGFR tyrosine phosphorylation in CHO cells. CHO cells were transfected with pRK5 EGFR expression vector and empty or RPTP-κ vector. One day after transfection, cells were mock (No UV) or UV irradiated (50 mJ/$cm^2$). Whole cell lysates were prepared 10 min post-treatment and subjected to Western analysis for total EGFR and tyrosine-phosphorylated EGFR. Levels of immunoreactive EGFR were quantified by chemifluorescent detection. Results are mean±S.E. of three independent experiments; *, p<0.05. Inset shows a representative image of chemifluorescent immunoreactive bands.

Transient transfection of CHO cells with EGFR expression vector resulted in high level of constitutive (i.e., in the absence of ligand) EGFR tyrosine phosphorylation (FIG. 2). This constitutive EGFR tyrosine phosphorylation was abolished by specific EGFR tyrosine kinase inhibitor PD169540, indicating tyrosine phosphorylation was due to intrinsic tyrosine kinase activity (data not shown). Also shown in FIG. 2, exposure of EGFR-expressing CHO cells to UV irradiation did not further increase EGFR tyrosine phosphorylation. However, co-expression of EGFR with RPTP-κ substantially reduced EGFR tyrosine phosphorylation. UV irradiation of CHO cells expressing both EGFR and RPTP-κ increased the level of EGFR tyrosine phosphorylation to the level observed in the absence of RPTP-κ (FIG. 2). These data demonstrate that RPTP-κ is required for UV irradiation induction of EGFR tyrosine phosphorylation, in the CHO cell model system.

RPTP-κ has a role in UV irradiation regulation of EGFR tyrosine phosphorylation in human keratinocytes. In addition to expressing both EGFR and RPTP-κ, keratinocytes express several EGFR ligands, including transforming growth factor-alpha (TGF-α), amphiregulin, HB-EGF, betacellulin, and epiregulin. To examine potential involvement of ligand-binding in UV irradiation induction of EGFR tyrosine phosphorylation, a neutralizing monoclonal antibody that blocks ligand binding to EGFR was used.

With reference to FIG. 3, UV-induced EGFR tyrosine phosphorylation is shown to be ligand-independent and mediated by oxidative inhibition of RPTP-κ in primary human keratinocytes. Shown in panel A, primary human keratinocytes were treated with control $IgG_1$ or EGFR antibody LA1 (1 µg/mL), which blocks ligand binding, as indicated. Cells were then treated with vehicle (CTRL), or EGF (10 ng/mL) for 10 min, or UV irradiated (50 mJ/cm$^2$) and harvested 15 min post irradiation. Whole cell lysates were subjected to Western analysis for total EGFR and tyrosine-phosphorylated EGFR. Levels of immunoreactive EGFR were quantified by chemifluorescent detection. Results are mean±S.E. of three independent experiments; *, p<0.05. Inset shows a representative image of chemifluorescent immunoreactive total and phospho-EGFR proteins. Shown in panel B, human keratinocytes were UV-irradiated (50 mJ/cm$^2$), and whole cell lysates were prepared at the indicated times. RPTP-κ and β-actin (internal control) were detected by Western blot, and quantified by chemifluorescent detection. Results are mean±S.E. of three independent experiments; *, p<0.05. Inset shows a representative image of chemifluorescent immunoreactive RPTP-κ and β-actin proteins. Shown in panel C, primary human keratinocytes were mock (No UV) or UV irradiated (50 mJ/cm$^2$), and whole cell lysates were prepared 5 min post-UV irradiation. RPTP-κ was immunoprecipitated, and phosphatase activity was determined using a tyrosine-phosphorylated EGFR peptide as substrate. Phosphatase activity was normalized to RPTP-κ protein content in the immunoprecipitates, which was quantified by Western analysis using chemifluorescent detection. Results are mean±S.E. of three independent experiments; *, p<0.05. Shown in panel D, primary human keratinocytes were mock or UV-irradiated (50 mJ/cm$^2$), and whole cell lysates were prepared in buffer containing iodoacetic acid (IAA, 10 mM) to irreversibly inhibit non-oxidized protein-tyrosine phosphatase activity, 5 min post-UV irradiation. Endogenous RPTP-κ was immunoprecipitated, and assayed for activity in buffer containing dithiothreitol to reduce oxidized RPTP-κ to restore enzymatic activity, using a tyrosine-phosphorylated EGFR peptide as substrate. Results are mean±S.E. of three independent experiments; *, p<0.05. Shown in panel E, RPTP-κ was immunoprecipitated from mock or UV-irradiated human keratinocytes, and the immunoprecipitates were treated with DTT to reduce oxidized RPTP-κ, as described above for panel C. Reduced RPTP-κ was irreversibly oxidized by pervanadate, and oxidized (OX-PTP) and total RPTP-κ were detected by Western blot, using specific antibodies. Results are mean±S.E. of three independent experiments; *, p<0.05. Inset shows a representative image of chemifluorescent immunoreactive total and oxidized RPTP-κ protein.

Figure 3A:
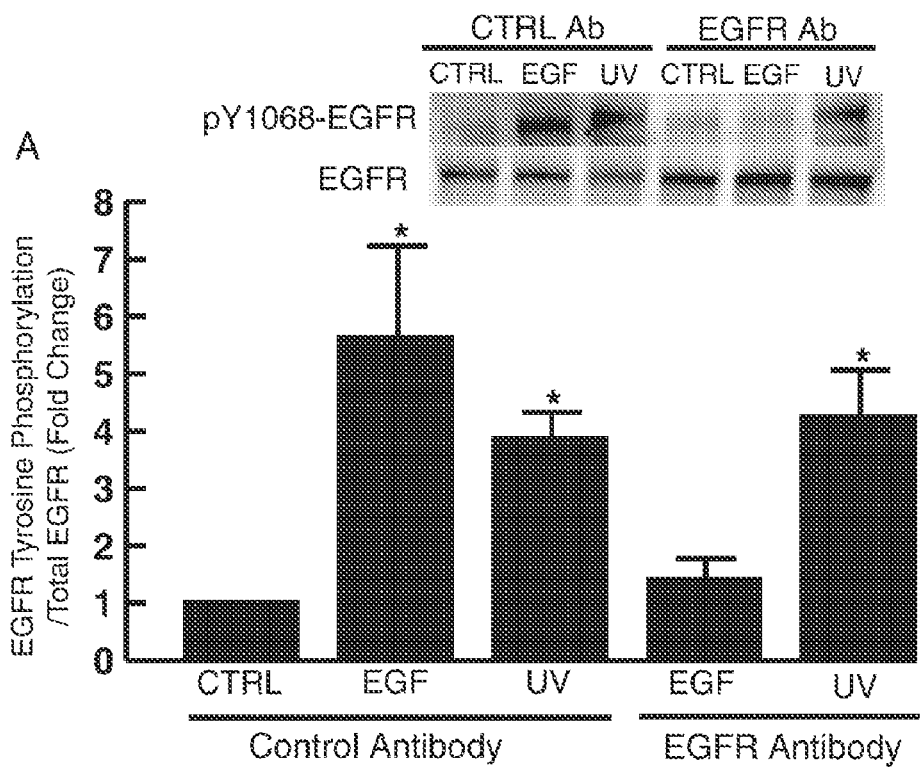
FIGS. 3A-E depict the results of experiments with primary human keratinocytes, where

While the EGFR antibody LA1 reduced EGF-induced EGFR tyrosine phosphorylation to near basal levels, it had no significant effect on UV irradiation induction of EGFR tyrosine phosphorylation (FIG. 3A). This result indicates that ligand-binding has little, if any, role in activation of EGFR by UV irradiation. This conclusion is consistent with the model that the EGFR ligand-binding domain is not required for UV irradiation induction of EGFR tyrosine phosphorylation.

Figure 3B:
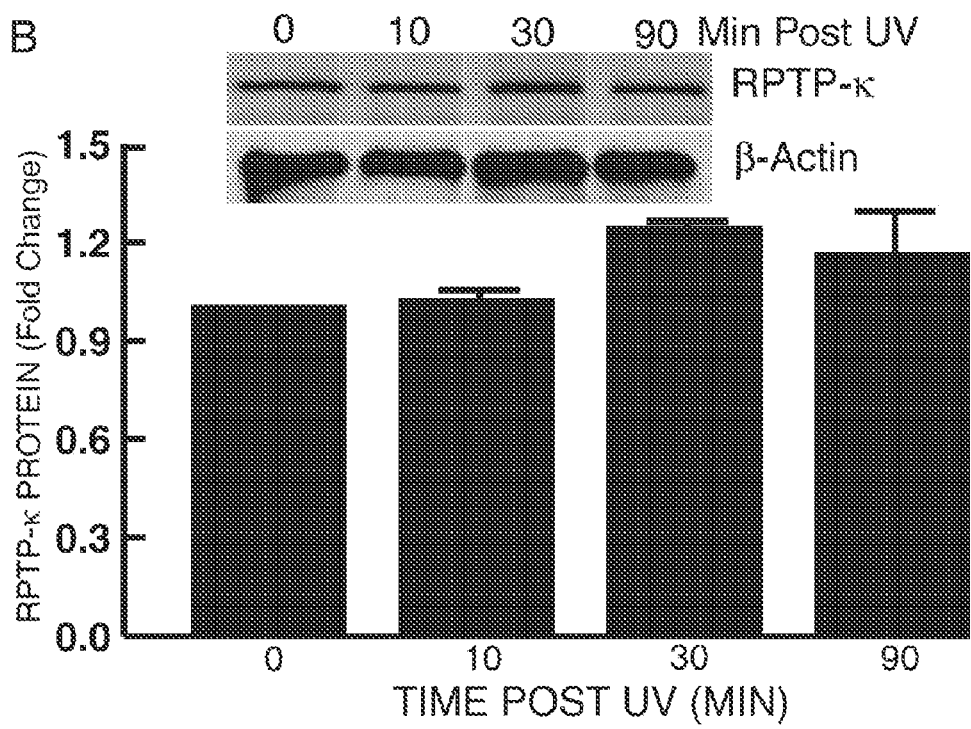
Figure 3C:
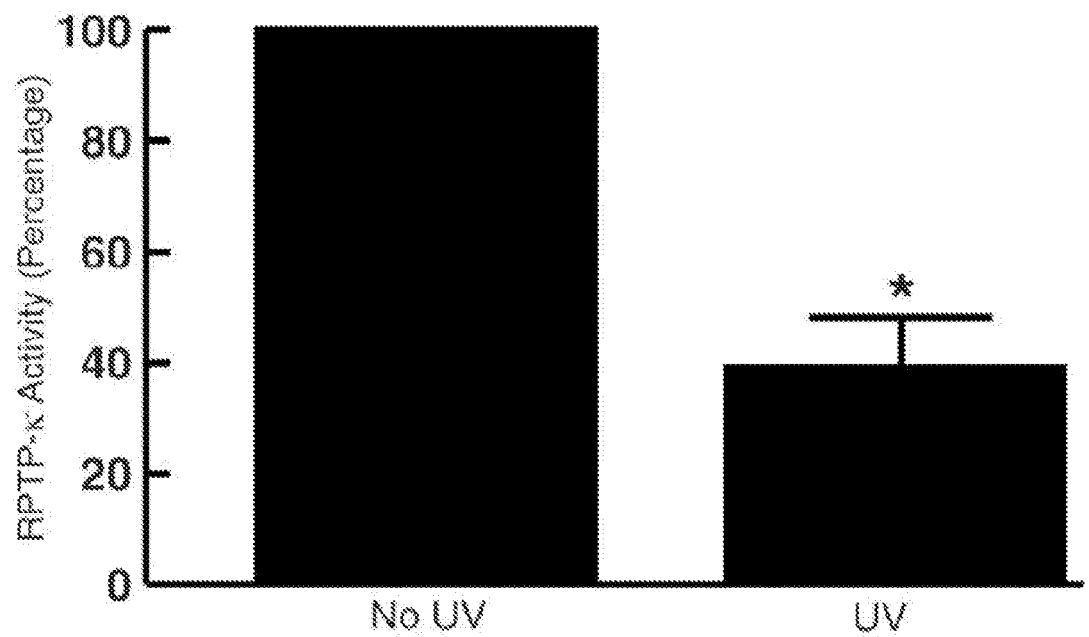

The experiments also determined whether UV irradiation altered RPTP-κ expression in human keratinocytes. No changes in RPTP-κ protein levels following UV irradiation were found (FIG. 3B). Accordingly, further examination was made into the effect of UV irradiation on RPTP-κ activity in human keratinocytes. For these studies, keratinocytes were mock-exposed or exposed to UV irradiation (50 mJ/cm$^2$) and harvested in lysis buffer five minutes post UV irradiation. RPTP-κ was immunoprecipitated, and its activity measured by dephosphorylation of a phosphotyrosine-containing synthetic peptide substrate, derived from the amino acid sequence of the EGFR (amino acids 1164-1176). UV irradiation reduced RPTP-κ activity in human keratinocytes more than 60%, compared to mock-irradiated cells (FIG. 3C). Although UV irradiation has been reported to reduce protein levels of PTP 1B and LAR in certain cell types though activation of proteolytic cleavage, no reduction of RPTP-κ protein level in human keratinocytes was found within 90 minutes following UV irradiation (data not shown).

Figure 3D:
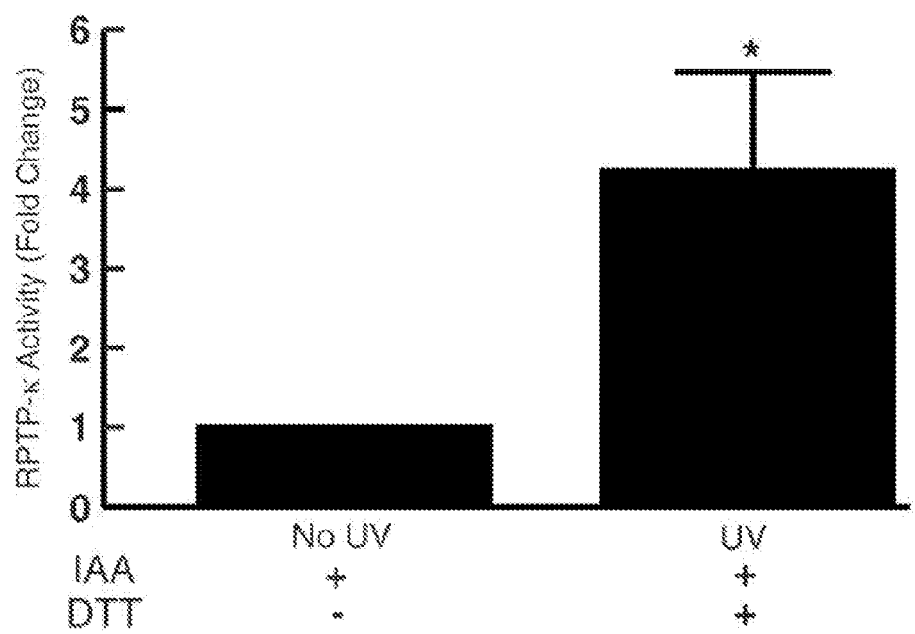

These data therefore indicate that UV irradiation inhibits RPTP-κ activity in human keratinocytes. To determine whether inhibition results from oxidation, iodoacetic acid was included in the lysis buffer that was used to harvest cells following mock or UV irradiation. Iodoacetate forms a stable adduct with non-oxidized, but not with oxidized, cysteine thiols. Therefore nonoxidized RPTP-κ is irreversibly inhibited by iodoacetate, whereas oxidized RPTP-κ is not. The activity of oxidized, but not acetylated, RPTP-κ can be restored by reduction with DTT. Immunoprecipitates from mock-irradiated keratinocytes, prepared in the presence of iodoacetate, and treated with DTT, contained four times less RPTP-κ activity, compared with immunoprecipitates from UV-irradiated cells (FIG. 3D). These data indicate that UV irradiation caused oxidation of RPTP-κ, which protected it against acetylation, in human keratinocytes.

Figure 3E:
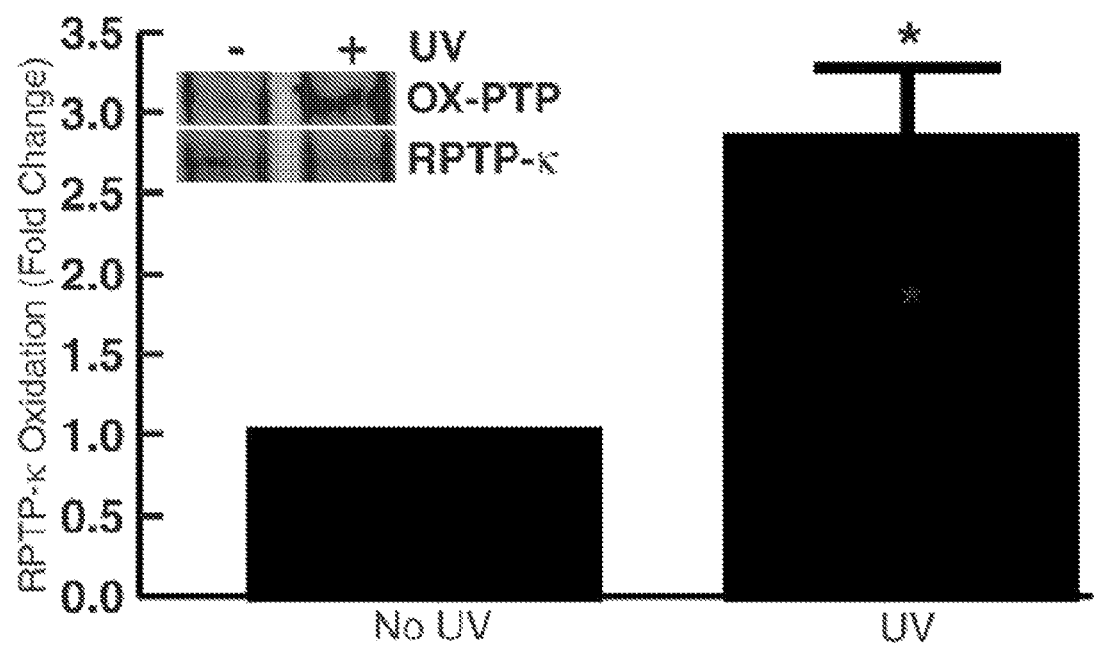

To confirm that UV irradiation leads to oxidation of RPTP-κ in human keratinocytes, an antibody that specifically recognizes the oxidized active site of protein-tyrosine phosphatases was utilized. RPTP-κ was immunoprecipitated from keratinocytes following mock exposure or exposure to UV irradiation. Immunoprecipitated RPTP-κ was analyzed for active site oxidation by Western analysis. The level of oxidized RPTP-κ was increased 3-fold in UV-irradiated, compared with non-irradiated keratinocytes (FIG. 3E).

Expression of exogenous RPTP-κ confers UV irradiation induction of EGFR tyrosine phosphorylation, in CHO cells (FIG. 2). Keratinocytes, however, express endogenous RPTP-κ. Therefore, siRNA-mediated knockdown was utilized to examine the role of RPTP-κ in UV irradiation regulation of EGFR tyrosine phosphorylation.

With reference to FIG. 4, knockdown of RPTP-κ is shown to increase EGFR tyrosine phosphorylation in primary human keratinocytes. Shown in panel A, human keratinocytes were transfected with scrambled control (CTRL) or RPTP-κ siRNA. Two days post-transfection, whole cell lysates were prepared and analyzed for RPTP-κ and β-actin (internal control) proteins by Western blot. Results are mean±S.E. of three independent experiments; *, p<0.05. Inset shows a representative image of chemifluorescent immunoreactive RPTP-κ and β-actin proteins. Shown in panel B, two days after transfection with control (CTRL) or RPTP-κ siRNA, keratinocytes were UV irradiated (50 mJ/cm2). Whole cell lysates were prepared 15 min post-UV irradiation and analyzed for total EGFR and tyrosine-phosphorylated EGFR Western blot. Results are mean±S.E. of three independent experiments; *, p<0.05. Inset shows a representative image of chemifluorescent immunoreactive total and phospho-EGFR (pY-EGFR) proteins. Shown in panel C, keratinocytes were transfected with control (CTRL) or RPTP-κ siRNA and treated with control IgG or neutralizing anti-EGFR antibody. Two days post-transfection, whole cell lysates were prepared and total and tyrosine-phosphorylated EGFR were quantified by ELISA. Results are mean±S.E. of three independent experiments; *, p<0.05.

Figure 4A:
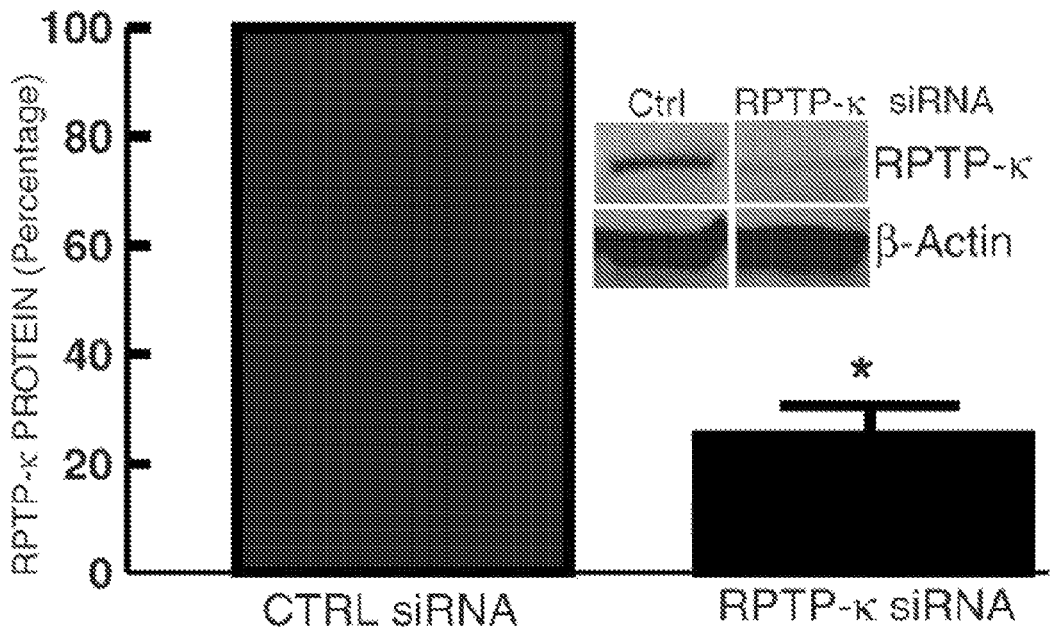
FIGS. 4A-C depict the results of experiments using primary human keratinocytes showing histograms of RPTP-κ protein levels after exposure to RPTP-κ siRNA and a control siRNA (4A), EGFR tyrosine phosphorylation with RPTP-κ siRNA before and after UV irradiation (4B), and the same with an EGFR antibody (4C), and Western blots of RPTP-κ for each (for 4A and 4B)
Figure 4B:
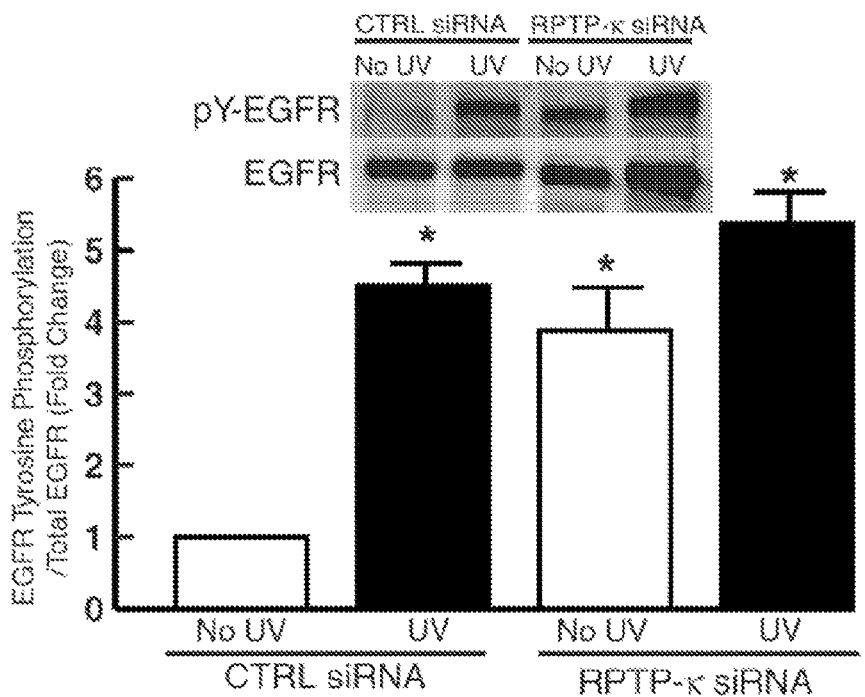
Figure 4C:
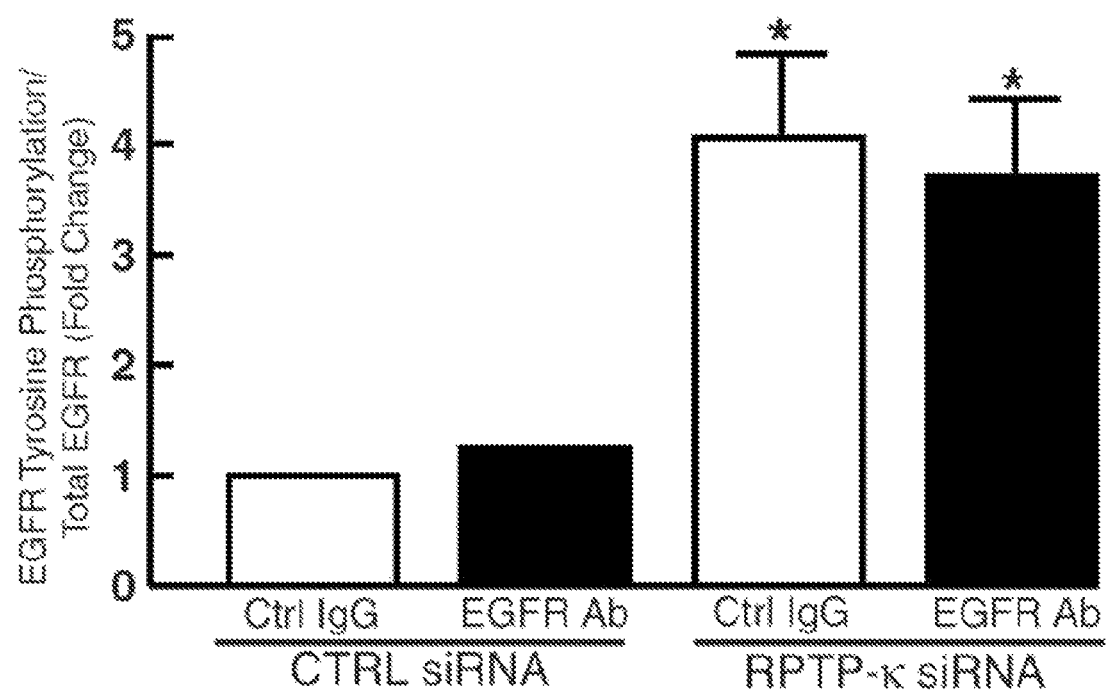

Transient transfection of RPTP-κ siRNA caused 80% and 70% reduction of RPTP-κ mRNA and protein (FIG. 4A), respectively. Knockdown of RPTP-κ had no effect on gene expression levels of other related RPTPs expressed in keratinocytes (RPTP-μ, -β, -δ, or -ζ). UV irradiation induced EGFR tyrosine phosphorylation nearly 5-fold in keratinocytes transfected with scrambled control siRNA (FIG. 4B), similar to that observed in nontransfected keratinocytes (FIG. 3). Knockdown of RPTP-κ increased EGFR tyrosine phosphorylation in non-irradiated keratinocytes nearly 4-fold. Exposure to UV irradiation further increased EGFR tyrosine phosphorylation only 20% (FIG. 4B). Addition of EGFR antibody that blocks ligand binding had no effect on increased EGFR tyrosine phosphorylation induced by RPTP-κ knockdown (FIG. 4C). These data indicate that normal levels of RPTP-κ function to maintain low basal EGFR tyrosine phosphorylation. In the presence of reduced levels of RPTP-κ, basal EGFR tyrosine phosphorylation is increased, and therefore can only be marginally further increased by UV irradiation. In the presence of normal levels of RPTP-κ, basal EGFR tyrosine phosphorylation is low, and oxidative inhibition of RPTP-κ by UV irradiation alters the EGFR tyrosine kinase/phosphatase balance to elevate EGFR tyrosine phosphorylation.

UV irradiation can damage skin cells, and with sufficient damage, induce apoptosis. In human keratinocytes, EGFR protects against UV-induced apoptosis, primarily through activation of the phosphatidylinositol 3-kinase/ATK pathway. Therefore, whether overexpression of RPTP-κ could modulate UV irradiation-induced DNA fragmentation (a marker of apoptosis) in human keratinocytes was examined.

Figure 5:
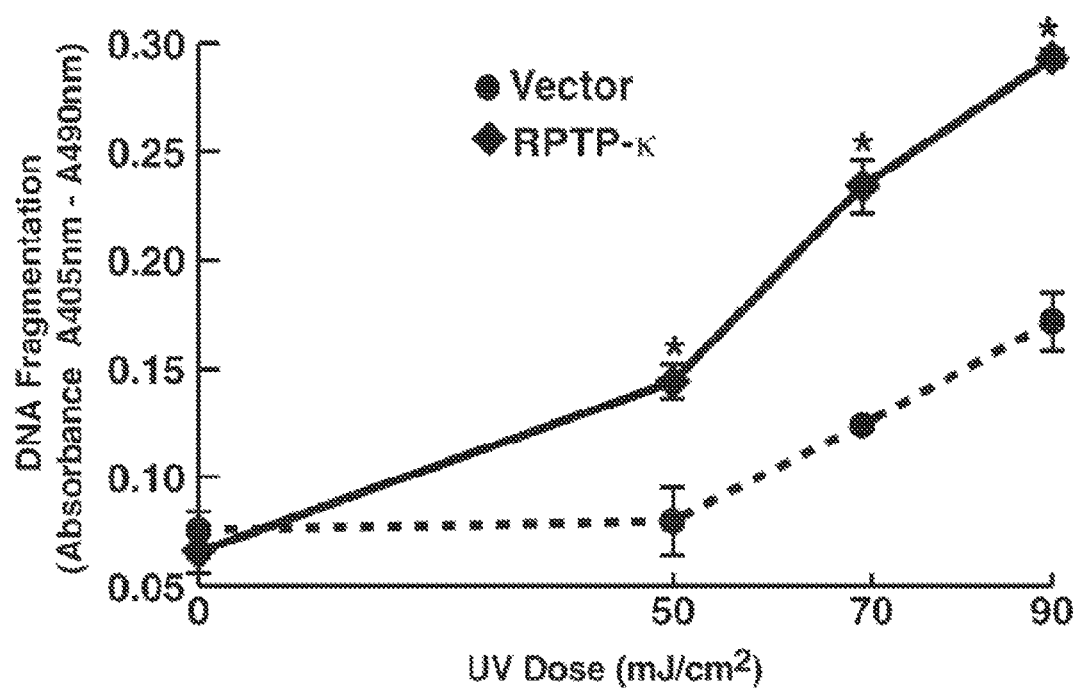
FIG. 5 depicts the results of experiments performed with primary human keratinocytes showing over-expression of RPTP-κ in UV-irradiated keratinocytes causes increased programmed cell death (apoptosis), measured as an increase in DNA fragmentation.

With reference to FIG. 5, RPTP-κ is shown to enhance UV irradiation-induced DNA fragmentation. Human primary keratinocytes were infected with either empty or RPTP-κ adenovirus. Cells were mock or UV irradiated 2 days post-infection. Six hours post-UV irradiation, cells were lysed, and DNA fragmentation was measured by ELISA. Results are mean±S.E. of three independent experiments; *, p<0.05 RPTP-κ versus empty vector.

At a dose of 50 mJ/cm$^2$, UV irradiation did not cause significant DNA fragmentation, compared with mock irradiation, in keratinocytes infected with control vector (FIG. 5). In contrast, this dose of UV irradiation causes a significant increase of DNA fragmentation in keratinocytes overexpressing RPTP-κ (FIG. 5). Higher doses of UV irradiation (70-90 J/cm$^2$) caused increased DNA fragmentation in both control and RPTP-κ overexpressing cells. However, increased expression of RPTP-κ caused increased levels of DNA fragmentation, at all doses of UV irradiation.

RPTP-κ expression and regulation by UV irradiation in human skin in vivo is illustrated as follows. Epidermis primarily consists of stratified layers of keratinocytes. The lowest layer of keratinocytes (basal keratinocytes) undergoes cell division. Daughter cells (suprabasal keratinocytes) migrate upward towards the surface, and, as they migrate, undergo a coordinated complex program of maturation. Suprabasal keratinocytes normally do not proliferate.

With reference to FIG. 6, localization of RPTP-κ and inhibition of RPTP-κ activity by UV irradiation of human skin in vivo is illustrated. Shown in panel A, is RPTP-κ mRNA expression in human epidermis, detected by in situ antisense probe hybridization. Sense probe served as control for specificity of hybridization. Shown in panel B, RPTP-κ protein expression in human epidermis, detected by immunohistochemistry. Preimmune serum and neutralization of RPTP-κ antibody (Ab) with immunogenic peptide were used as controls for specificity of staining. Shown in panel C, co-localization of EGFR (green) and RPTP-κ (red) proteins in human epidermis, detected by double immunofluorescence staining. Shown in panel D, sun-protected buttocks skin of human subjects was exposed to twice the minimal erythema dose of UV irradiation. Samples from non-irradiated and UV-irradiated skin were obtained 30 min post-irradiation. RPTP-κ was immunoprecipitated and analyzed by Western blot, using chemifluorescent detection. Results are mean±S.E. of five independent experiments. Shown in panel E, RPTP-κ in immunoprecipitates obtained from non-irradiated and UV-irradiated human skin, as described for panel D, were assayed for activity, using a tyrosine-phosphorylated EGFR peptide as substrate. Results are mean±S.E. of three independent experiments; *, p<0.05. Color versions of panels A, B, and C are found in Xu et al., J. of Biol. Chem, Vol. 281, No. 37, pp. 27389-27397, Sep. 15, 2006.

Figure 6A:
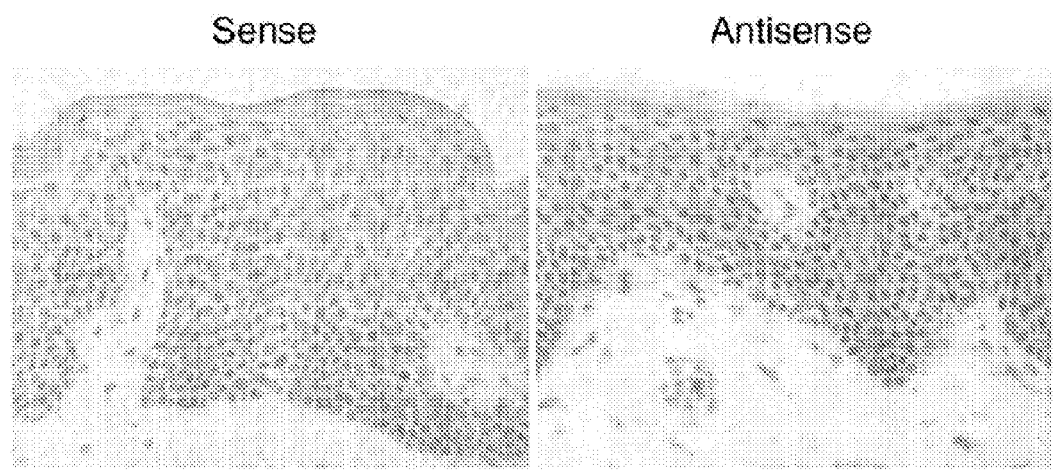
FIGS. 6A-E depict results of in vivo experiments showing localization of RPTP-κ and the effect of UV irradiation on RPTP-κ activity and RPTP-κ protein content in human skin, where
Figure 6B:
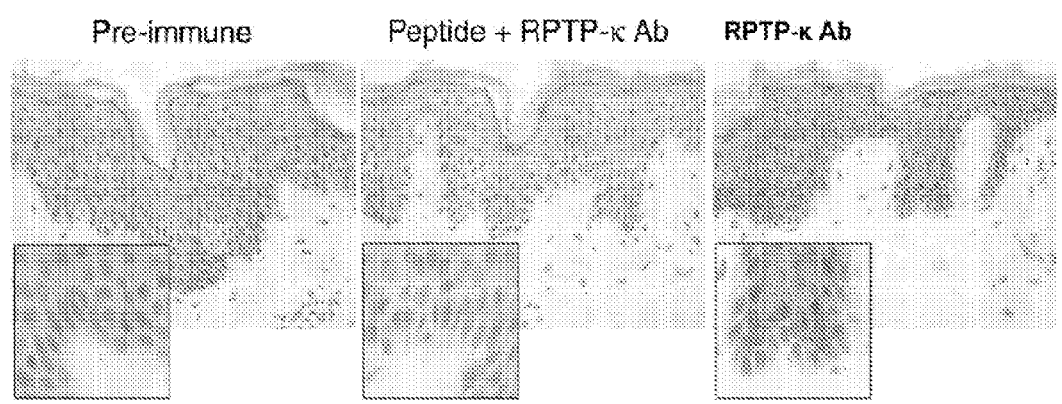
Figure 6C:
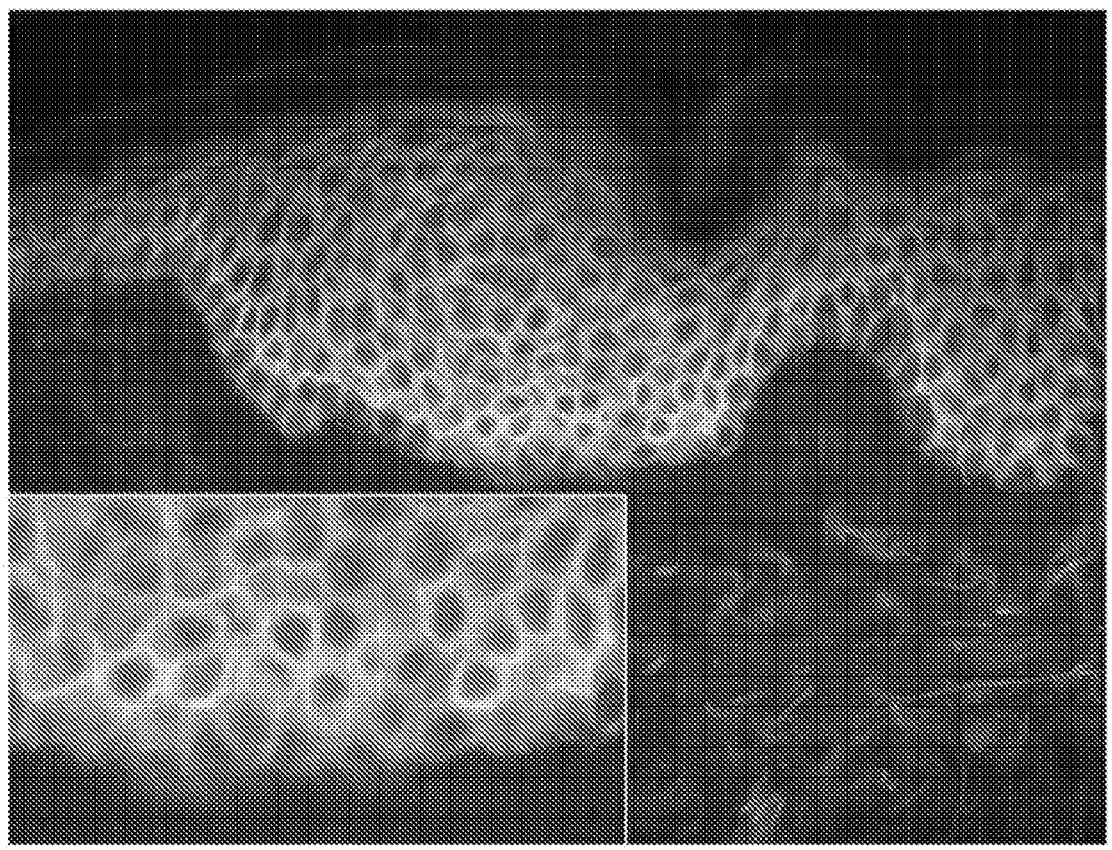
Figure 6D:
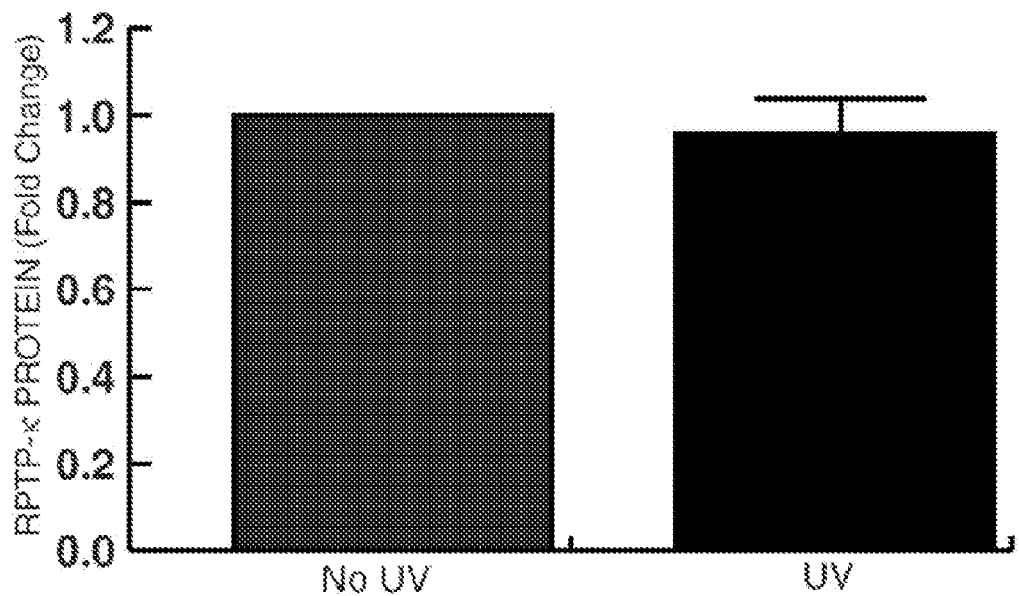

It was discovered that RPTP-κ mRNA is expressed predominantly in suprabasal keratinocytes (FIG. 6A). A similar pattern of expression for RPTP-κ protein is observed (FIG. 6B). EGFR protein, the substrate for RPTP-κ, was expressed throughout the epidermis in both basal and suprasbasal keratinocytes (FIG. 6C). Erk MAP kinase is a major EGFR effector in many cells, including human keratinocytes. UV irradiation activates Erk1/2 in human keratinocytes in skin in vivo, and this activation is dependent on EGFR. In view of the experiments described herein, the observation that the localization of activated Erk closely coincides with that of RPTP-κ in UV irradiated human skin can now be explained by UV irradiation oxidative inhibition of RPTP-κ leading to EGFR-dependent Erk activation of suprabasal keratinocytes in human skin in vivo. EGFR is a major activator of the mitogenic pathway in basal keratinocytes. Accordingly, predominant expression of the inhibitor RPTP-κ in non-proliferating suprabasal keratinocytes is consistent with its role in limiting EGFR tyrosine phosphorylation. The observation by Xu, Y et al. (2005) *J. Biol. Chem.* 280, 42694-42700 that overexpression of RPTP-κ in cultured basal keratinocytes completely inhibits proliferation provides additional support for this notion.

Figure 6E:
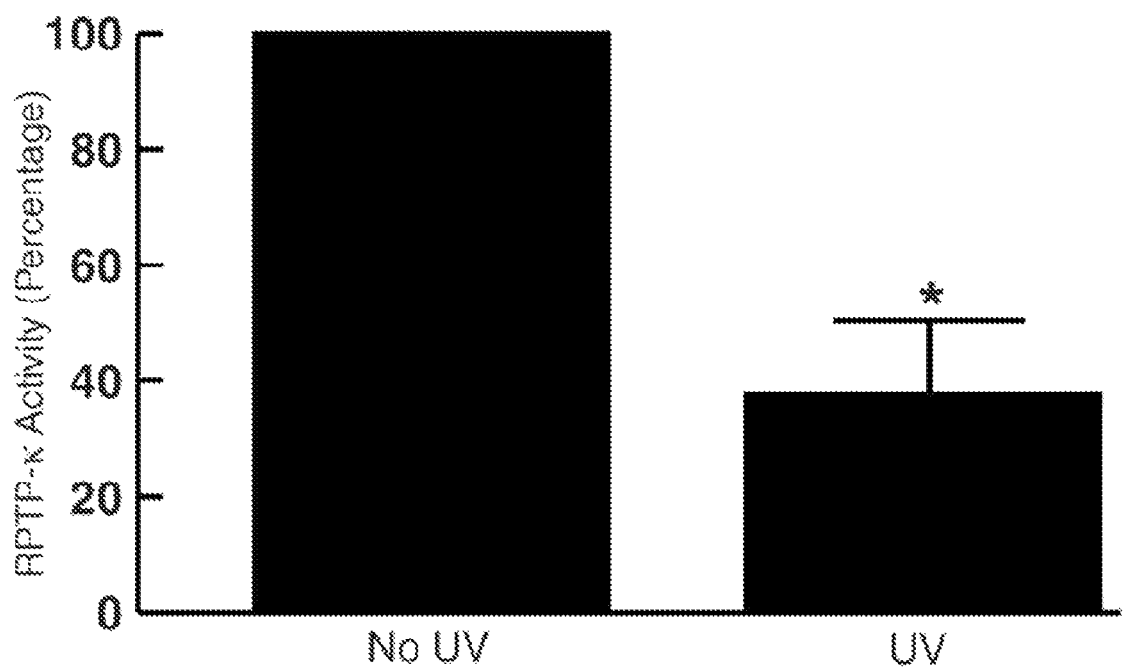

Exposure of human skin in vivo to UV irradiation increases EGFR tyrosine phosphorylation, as described by Fisher, G., et al. (1998) *J Clin Invest* 101, 1432-1440). Increased tyrosine phosphorylation was maximal (5-fold) 30 minutes after exposure (ibid.). To determine the effect of UV irradiation on RPTP-κ, sun-protected buttock skin of human adult subjects was exposed to UV irradiation, and skin samples were obtained 30 minutes post exposure. UV irradiation had no effect on RPTP-κ protein level in human skin in vivo (FIG. 6D), consistent with the effects observed in cultured keratinocytes (FIG. 3B). In contrast, UV irradiation inhibited RPTP-κ activity more than 60% (FIG. 6E). These results are similar to those obtained in cultured keratinocytes, and provide support for RPTP-κ as a critical regulator of EGFR tyrosine phosphorylation in UV-irradiated human skin in vivo.

Activation of signal transduction cascades and concomitant alterations in genes that occur in skin cells in response to exposure to UV irradiation are largely dependent on increased EGFR tyrosine phosphorylation. In human skin, EGFR-dependent responses are critical elements in the pathophysiology of UV irradiation induced cancer and aging. Currently, with the exception of sunscreens, there are no effective measures for preventing these serious solar UV irradiation-induced skin conditions. The present data demonstrate that oxidative inhibition of RPTP-κ is a central mechanism by which UV irradiation activates EGFR in human skin. Anti-oxidants, as topical preparations or dietary supplements, have gained popular attention with claims for a multiplicity of health benefits. However, these claims have been difficult to substantiate. One reason for this difficulty is lack of specific molecular targets for assessment of anti-oxidant effect. The present disclosure identifies RPTP-κ as a key molecular target for anti-oxidant action for prevention of the primary manifestations of solar UV irradiation induced skin damage.

As such, the present disclosure provides in vitro and in vivo methods for selection and application of treatments and compounds that are operable to protect RPTP-κ activity from oxidation mediated by UV irradiation or any other insult. Protection of RPTP-κ activity may prevent or reduce the effects of photoaging and UV irradiation damage to cells.

Regardless the insult, measurement of RPTP-κ levels and activities before and after challenge by the insult can be used to ascertain whether the insult is actually detrimental to the natural, endogenous EGFR signaling that is attenuated by RPTP-κ activity. If the insult is detrimental, measurement of the same with and without a candidate treatment or composition can screen for therapeutically useful treatments and/or compositions.

An "insult" is something that causes or has potential to cause injury to body tissues and as used herein means any phenomenon or compound that generates reactive oxygen species, such as peroxides, or otherwise inhibits RPTP-κ, directly or indirectly. UV irradiation and various compounds (e.g., $H_2O_2$) can cause the formation of reactive oxygen species. This includes endogenous compounds such as NADPH oxidase, which is normally latent in neutrophils and is used by those cells to generate superoxide in phagosomes to degrade ingested bacteria and fungi. Compounds such as Paraquat (N,N'-dimethyl-4,4'-bipyridinium dichloride) and similar quaternary ammonium herbicides are easily reduced to a radical that generates superoxide. Additionally, treatment of most cell types with growth factor or cytokine not only increases growth factor receptor activity, but also NADPH oxidase activity. The present disclosure thus enables determining whether a variety of insults inhibits the activity of RPTP-κ and the ability of RPTP-κ to dephosphorylate EGFR.

The present disclosure therefore provides methods for determining whether an insult affects RPTP-κ activity. These include providing cells expressing RPTP-κ and measuring initial RPTP-κ activity. The cells are then exposed to the insult and RPTP-κ activity again measured. The insult is identified as affecting RPTP-κ activity if the RPTP-κ activity measured after exposure to the insult is different than the RPTP-κ activity prior to the insult. The method may further employ cells that also express EGFR. In this case, initial EGFR phosphorylation is measured and EGFR phosphorylation is again measured after exposure to the insult. The insult is then identified as inhibiting RPTP-κ activity if RPTP-κ activity measured after exposure to the insult is decreased relative to initial RPTP-κ activity prior to the insult and EGFR phosphorylation is increased relative to initial EGFR phosphorylation. The insult may be UV irradiation and the cells may be cultured cells. Measuring RPTP-κ activity may include at least one of measuring the oxidative state of RPTP-κ and measuring phosphatase activity of RPTP-κ.

Another method for the identification of an insult includes the following. With respect to the procedures described herein, EGFR tyrosine phosphorylation, RPTP-κ levels, and/or RPTP-κ activity of transfected CHO cells are measured before and after exposure of the cells to an insult (e.g., UV irradiation, reactive oxygen species, etc.). A statistically significant increase in EGFR phosphorylation or decrease in RPTP-κ levels or activity indicates that the insult is detrimental to RPTP-κ and/or an EGFR activator.

Having identified an insult, the present disclosure provides methods for determining whether a treatment and/or composition protect RPTP-κ activity from the insult. A cell having a known RPTP-κ activity is provided and the composition is administered to the cell. The cell is exposed to the insult and activity of the RPTP-κ in the cell after exposure to the insult is measured. The composition is identified as protecting RPTP-κ activity if the measured activity of the RPTP-κ in the cell after exposure to the insult is about the same as the known RPTP-κ activity or RPTP-κ activity before the insult. The RPTP-κ protein level in the cell may be measured after exposure to the insult.

Another method for evaluating a treatment and/or composition includes the following. Having followed the present methods and procedures, or otherwise identifying an insult that inhibits RPTP-κ activity, and having a candidate treatment or composition, the experimental procedures as described with respect to FIG. 3 may be used (analogous to the use of DTT) where RPTP-κ activity is measured with and without the candidate compound, optionally at varying doses, after exposure to UV. A cell free assay may be used to determine if RPTP-κ is inhibited, and whether a candidate compound protects RPTP-κ from oxidate inactivation. High throughput screening (HTS), a well-known automated screening method, can be used with cells or in a cell free manner to screen for compounds that inhibit RPTP-κ and for compounds that protect RPTP-κ activity. After the candidate compound is confirmed as protecting RPTP-κ in the presence of the insult, it can be formulated into a form suitable for a desired route of administration.

As another example, the present methods demonstrate that *Laminaria japonica* extract inhibits UV irradiation-induced EGFR activation in human primary keratinocytes. Several candidate treatments and compounds are examined for their affect on RPTP-κ activity and/or EGFR phosphorylation. The present methods have been applied to *Laminaria japonica* extract (LJE), *Porphyra haitanensis* (PHE) extract, or resveratrol (RV). The LJE and PHE are prepared by grinding each seaweed into a particulate form and performing liquid phase extractions. Various organic and aqueous solvents can be used to prepare extracted material, for example, alcohol such as methanol, organic solvent such as hexane, and water were used to prepare extracts from *Laminaria japonica* and *Porphyra haitanensis*. In the case of *Laminaria japonica*, extraction with methanol was found to contain activity that inhibits UV irradiation-induced EGFR activation. Preparations of aqueous LJE and hexane LJE did not contain the same extent of activity. None of the methanol, aqueous, and hexane extracts of *Porphyra haitanensis* contained such activity. Likewise, resveratrol did not exhibit activity that inhibits UV irradiation-induced EGFR activation.

The various extracts may be used as is or may be concentrated, for example, by filtration or evaporation of liquid. The various extracts may be dried under vacuum (e.g., freeze dried or lyophilized) and the residue may be resuspended in or mixed with a different vehicle or solvent. For example, the methanol extract can be lyophilized and resuspended in an aqueous buffer. Alternatively, the dried or partially dried extract may be resuspended in a vehicle for topical application to skin, such as a lotion, cream, or ointment. These vehicles may be further formulated with other ingredients into sunscreens, for example.

Sunscreens that contain *Laminaria japonica* extract may include ingredients listed in the FDA monograph, listed in Table 1.

TABLE 1

FDA Sunscreen Final Monograph Ingredients

| Drug Name | Concentration, % | Absorbance |
|---|---|---|
| Aminobenzoic acid | Up to 15 | UVB |
| Avobenzone | 2-3 | UVAI |
| Cinoxate | Up to 3 | UVB |
| Dioxybenzone | Up to 3 | UVB, UVAII |
| Ecamsule | 2 | UVAII |
| Ensulizole | Up to 4 | UVB |
| Homosalate | Up to 15 | UVB |
| Meradimate | Up to 5 | UVAII |
| Octocrylene | Up to 10 | UVB |
| Octinoxate | Up to 7.5 | UVB |
| Octisalate | Up to 5 | UVB |
| Oxybenzone | Up to 6 | UVB, UVAII |
| Padimate O | Up to 8 | UVB |
| Sulisobenzone | Up to 10 | UVB, UVAII |
| Titanium dioxide | 2 to 25 | Physical |
| Trolamine salicylate | Up to 12 | UVB |
| Zinc oxide | 2 to 20 | Physical |

The following methods and experiments were performed using material prepared from the methanol extracts of *Laminaria japonica* and *Porphyra haitanensis*.

Figure 7:
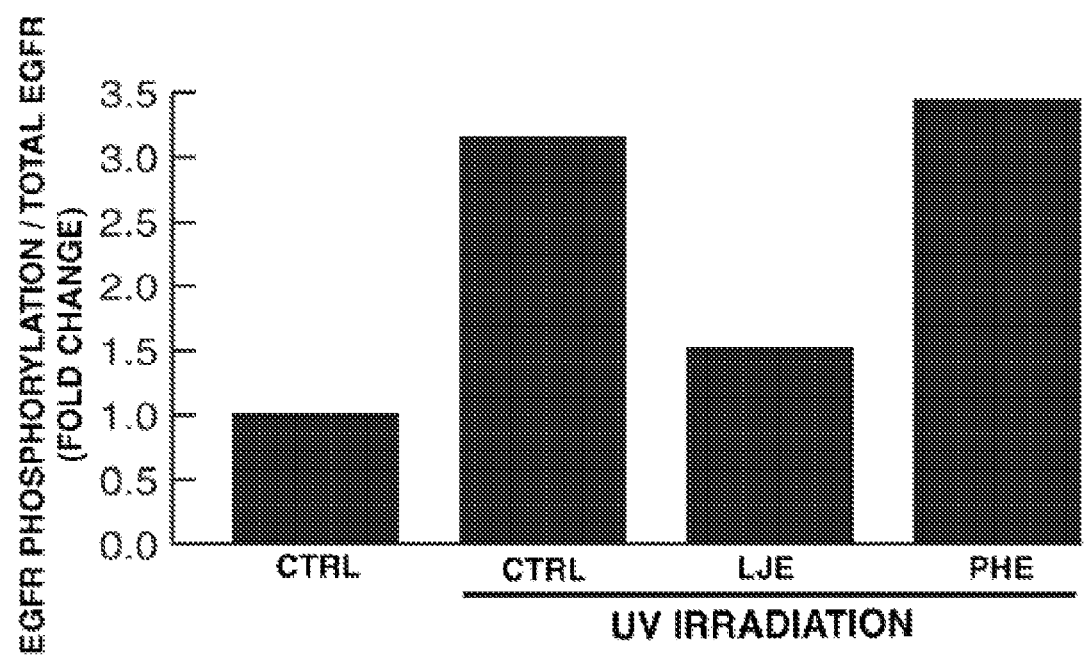
FIG. 7 depicts a histogram illustrating the ratio of EGFR phosphorylation to total EGFR in keratinocytes treated with no extract (CTRL), *Laminaria japonica* extract (LJE), or *Porphyra haitanensis* extract (PHE) and exposed to UV irradiation.

With reference to FIG. 7, primary adult human keratinocytes were treated with *Laminaria japonica* extract (LJE) or *Porphyra haitanensis* extract (PHE) for 16 hours prior to exposure to ultraviolet (UV) irradiation (50 mJ/cm2). Cells were analyzed for phosphorylated epidermal growth factor receptor (EGFR) and total EGFR by Western analyses 30 minutes post irradiation.

Figure 8:
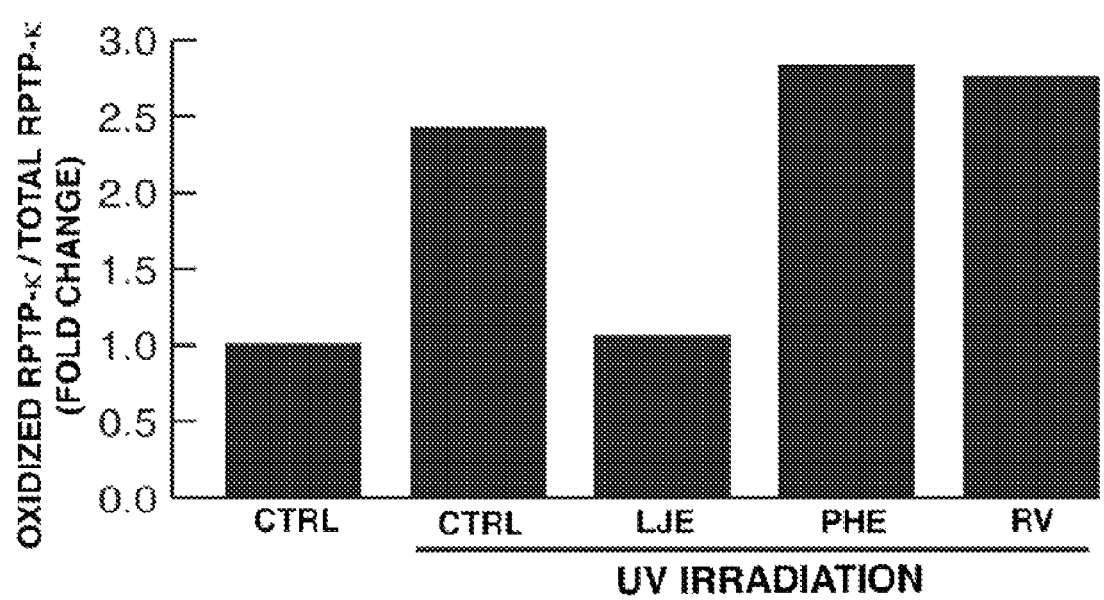
FIG. 8 depicts a histogram illustrating the ratio of oxidized RPTP-κ to total RPTP-κ in keratinocytes treated with no extract (CTRL), *Laminaria japonica* extract (LJE), or *Porphyra haitanensis* extract (PHE) and exposed to UV irradiation.

With reference to FIG. 8, primary adult human keratinocytes were treated with *Laminaria japonica* extract (LJE), *Porphyra haitanensis* (PHE) extract, or resveratrol (RV) for 16 hours prior to exposure to ultraviolet (UV) irradiation (100 mJ/cm$^2$). Cells were analyzed for oxidized receptor protein tyrosine phosphatase-kappa (RPTP-κ) and total RPTP-κ by Western analyses 10 minutes post irradiation.

Figure 9:
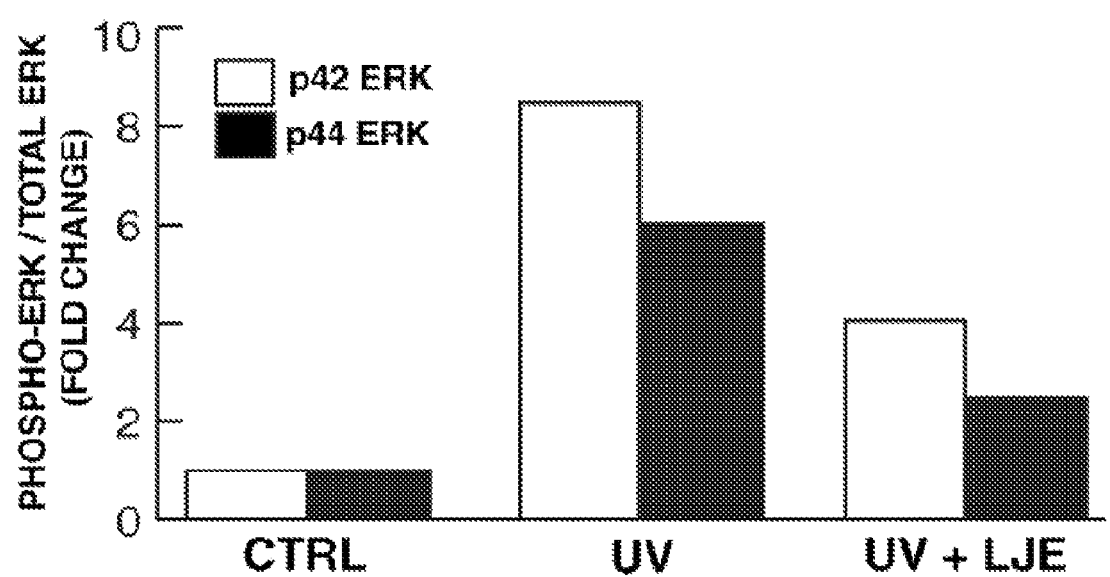
FIG. 9 depicts a histogram illustrating the ratio of phosphorylated ERK to total ERK in keratinocytes treated with no extract (CTRL), *Laminaria japonica* extract (LJE), or *Porphyra haitanensis* extract (PHE) and exposed to UV irradiation.

With reference to FIG. 9, primary adult human keratinocytes were treated with *Laminaria japonica* extract (LJE) for 16 hours prior to exposure to ultraviolet (UV) irradiation (50 mJ/cm$^2$). Cells were analyzed for ERK phosphorylation and total ERK by Western analyses 15 minutes post irradiation.

In addition, the present methods have been applied to demonstrate that certain antioxidants have no effect on UV-induced EGFR activation. Antioxidants which have no effect on UV-induced EGFR activation include: CAPE (Caffeic acid phenethyl ester), MCI-186 (3-Methyl-1-phenyl-2-pyrazolin-5-one), Resveratrol, Tocopherylquinone, d-alpha, Mito Q10, Bamboo water extract, *Porphyra haitanensis* extract, *Sargassum fusiforme* extract (3), Green tea extract (EGCG), and N-Acetyl cysteine (NAC) (data not shown).

The following description further illustrates materials and methods employed in the present disclosure.

Materials—Adult human primary keratinocytes were purchased from Cascade Biologics Inc. (Portland, Oreg.). Chinese hamster ovary (CHO) cells were obtained from ATCC. EGFR and Phospho-EGFR (pY1068) antibodies used for Western analysis were purchased from Santa Cruz Biotechnology (Santa Cruz, Calif.) and Cell Signaling Technology (Beverly, Mass.), respectively. EGFR antibody for immunofluorescence was from Neomarkers (Fremont, Calif.). Neutralizing EGFR antibody LA1 which blocks ligand-binding, was obtained from Upstate Biotechnologies (Waltham, Mass.). RPTP-κ antibody was generated and affinity purified from rabbits immunized with a peptide derived from the intracellular domain of human RPTP-κ (as described by Xu, Y et al. (2005) *J. Biol. Chem.* 280, 42594-42700). Phosphotyrosine peptide derived from EGFR (Biotin-KGSTAENAE (pY)LRV-amide) was synthesized by New England Peptide. Inc. (Gardner, Mass.). PD169540 is a generous gift from Dr. David Fry (Pfizer Inc.) Oligonucleotide probes used for in situ hybridization were synthesized by GeneDetect.com (Bradenton, Fla.). Purified, full length active human EGFR was obtained from BioMol (Plymouth Meeting, Pa.). Intracellular region of RPTP-κ was cloned into pGEX-6-P, and expressed as a HIS-tagged GST fusion protein in BL21. Expressed RPTP-κ was purified by nickel chelate and glutathione affinity chromatography to a purity of greater than 90%, as judged by SDS PAGE.

Cell culture—Subcultures of adult human primary keratinocytes were expanded in modified MCDB153 media (EpiLife, Cascade Biologics, Inc.) at 37° C. under 5% $CO_2$, CHO cells were cultured in Ham's F12 medium with 1.5 g/ml sodium bicarbonate, supplemented with 10% FBS under 5% $CO_2$, at 37° C.

UV source and irradiation—Subconfluent cells in a thin layer of Tris-buffered saline were irradiated using a Daavlin lamp apparatus containing six FS24T12 UVB-HO bulbs. A Kodacel TA401/407 filter was used to eliminate wavelengths below 290 nm (UVC) resulting in a UV spectrum consisting of 48% UVB, 31% UVA2 and 21 % UVA1. The irradiation intensity was monitored with an IL1400A phototherapy radiometer and a SED24O/UVB/W photodetector (International Light, Newbury, Mass.). Human subjects were phototested to determine the dose of UV irradiation that caused the skin to become slightly pink (MED=minimal erythema dose). Subjects were exposed to twice this dose for studies. All procedures involving human subjects were approved by the University of Michigan Institutional Review Board and all subjects provided written informed consent.

Transient transfection of CHO cells—Mammalian expression vectors harboring EGFR (pRK5 EGF) or RPTP-κ pShuttle RPTP-κ) coding sequences were transiently transfected by Lipofectamine 2000 method into CHO cells according to manufacturer's protocol (Invitrogen Corporation, Carisbad, Calif.).

siRNA silencing of endoqenous RPTP-k in primary human keratinocytes—A 21mer RNA sequence (5' AAG GTT TGC CGC TTC CTT CAG 3') derived from RPTP-κ coding sequence was designed using Oligoengine's software (Seattle, Wash.). Homology search was performed on this RNA sequence using Blast (http://www.ncbi.nlm.nih.gov/BLAST/) to ensure it was not presented in any other known sequence in the database. Double-stranded siRNA was synthesized by Qiagen-Xeragon Inc. (Valencia, Calif.). The synthetic siRNA was transfected into primary human keratinocytes using Human Keratinocytes Nucleofector kit and device from Amaxa Biosystems (Cologne, Germany) according to manufacturer's protocol.

RPTP-κ immunoprecipitation, protein tyrosine phosphatase assay, and EGFR tyrosine phosphorylation ELISA—Keratinocytes whole cell lysates were made in TGH buffer (50 mM Hepes, pH 7.2. 20 mM NaCl, 10% glycerol and 1% Triton X -100), supplemented with 10 µg/ml aprotinin, 10 µg/ml leupeptin. 10 µg/ml pepstatin A and 1 mM PMSF, and were pre-cleared with normal rabbit IgG before incubation with RPTP-k antibody for three hours at 4° C. For some assays 10 mM iodoacetic acid was added to TGH buffer to irreversibly inhibit non-oxidized protein tyrosine phosphatase activity (see Bae, Y., et al. (1997) J Biol Chem 272, 217-221). Protein A-conjugated agarose beads were then added, and further incubated at 4° C. for two hours, followed by extensive washing. Washed immunoprecipitates were analyzed by Western blot, or assayed for protein tyrosine phosphatase activity. For some assays 10 mM DTT was added to the assay buffer to reduce oxidized RPTP-κ (see Bae et al.). For measurement of protein phosphatase activity, tyrosine-phosphoryiated peptide derived from EGFR was added to a final concentration of 0.5 mM in 50 ml PTP assay buffer (50 µM Tris, pH 7.6, 100 µM NaCl, 100 µg/ml BSA). Reactions were terminated by addition of 100 µL of BIOMOL Green Reagent (BIOMOL, Plymouth Meeting, Pa.) and absorbance measured at 620 nm. Human total EGFR and tyrosine 1068 phospho-EGFR were quantified by ELISA (Biosource International, Camarillo, Calif.).

Western blot analysis of UV irradiation-induced oxidation of RPTP-κ in human primary keratinocytes—Human primary keratinocytes were mock irradiated or UV irradiated (90 mJ/cm$^2$). Five minutes post UV irradiation, cells were lysed in the presence of 100 mM Iodacetic acid, and RPTP-κ was immunoprecipiated as described above. The immunoprecipitate was reduced by addition of 10 mM dithiothreitol in TGH buffer, containing protease inhibitors, for 30 minutes at 4° C. The immunoprecipitate was washed three times, and then irreversibly oxidized by incubation with 2 mM pervanadate at 4° C. for one hour. Oxidized RPTP-κ was analyzed by Western blot probed with oxPTP antibody (A gift from Dr. Arne Ostman, Cancer Center Karolinska. Stockholm, Sweden; as described by Persson, C. et al. (2005) Methods 35, 37-43).

Western analysis detection and quantitation—Western blots were developed and quantified using a chemifluorescent substrate (ECF Western Blot Reagents, Amersham Biosciences, Arlington Heights, Ill.). Detection of chemifluorescense was performed using a STORM PhosphorImager (Molecular Dynamics, Sunnyvale, Calif.). Sample loads, antibody concentration, and incubator times were adjusted to yield fluorescent signals within the linear range of detection. Fluorescent intensity of protein bands were quantified by ImageQuant software, which is an integral application of the STORM.

Detection of UV irradiation-induced DNA fragmentation in human primary keratinocytes—Human primary keratinocytes were infected with either empty or RPTP-κ adenovirus. Cells were mock or UV-irradiated two days post infection. Six hours post UV irradiation, cells were lysed, and DNA fragmentation was measured by Cell Death Detection ELISA according to manufacturer's instructions (Roche Applied Science, Penzberg, Germany)

In situ hybridization—Hybridization buffer (4×SSC, 20% dextran sulfate, 50% formamide, 0.25 mg/ml salmon sperm DNA, 0.25 mg/ml yeast tRNA, 0.1M DTT, 0.5× Denhardt's solution) with three fluorescine-conjugated sense or antisense DNA oligonucleotide probes, corresponding to nucleotides 1549-1596, 3440-3487, and 4290-4337 in the human RPTP-κ mRNA sequence (genebank accession number NM_002844), at 37° C. overnight. Sections were washed in 2×PBS with 0.01% Tween 20, then 1×PBS. 0.01% Tween 20. Washed slides were incubated with protein block (Biogenex, San Ramon, Calif.), biotin-labeled anti-fluorescence antibody, followed by horse radish peroxidase-strepaviden. Hybridized probes were visualized by addition of AEC as substrate.

Immunohistology and immuno-fluorescence—Human full thickness skin samples were embedded in OCT and frozen in liquid nitrogen. Frozen sections (7 µm) were cut with a cryostat (LEICA CM3050). Sections were air dried for 10 minutes, fixed with 2% paraformaldehyde for 20 minutes at room temperature, and washed for 20 minutes. Slides were loaded on an automated immunostainer (Biogenex i6000). For immunoperoxidase staining, slides were incubated with peroxide block (10 minutes), protein block (20 minutes), rabbit affinity-purified anti-RPTP-κ (30 minutes), Multilink-biotin conjugate (10 minutes), streptaviden-conjugated horse radish peroxidase (10 minutes), AEC substrate (3 minutes), and Hemotoxylin (20 seconds). For double immunofluorescence, peroxide block was omitted, and following incubation with RPTP-κ antibody, biotin-conjugated anti-rabbit antibody (Vector Laboratories, Burlingame, Calif.), and streptavidin-conjugated AlexaFluor 594 (Invitrogen-Molecular Probes, San Diego, Calif.) were each added for 10 minutes. Slides were washed with distilled water, EGFR antibody (Ab-10) was added overnight at 4° C., and anti-mouse $IgG_1$-conjugated FITC (Caltag, Burlingame, Calif.) was added for 10 minutes. Stained slides were washed with distilled water, and covered with Supermount. For negative control, staining was performed using RPTP-κ antibody plus peptide used to raise the antibody, or pre-immune serum, instead of primary antibody. Staining was observed under a Zeiss microscope (Axioskop 2) and images were obtained with digital camera (SPOT2, Diagnostic Instruments, Inc., Sterling Heights, Mich.). All reagents, except as noted, were from Biogenex.

All referenced literature and patents are incorporated herein by reference. The examples and other embodiments described herein are exemplary and not intended to be limiting in describing the full scope of compositions and methods of the technology. Equivalent changes, modifications and variations of specific embodiments, materials, compositions, and methods may be made within the scope of the present technology, with substantially similar results.

What is claimed is:

1. A method for measuring whether a treatment affects RPTP-κ activity in a cell, comprising:
   providing cells expressing RPTP-κ;
   applying the treatment to at least one cell;

exposing treated and untreated cells to UV irradiation;

measuring the activity of RPTP-κ, wherein a difference in the activity of RPTP-κ following UV irradiation in the treated and untreated cells is indicative of the treatment affecting RPTP-κ activity.

2. The method of claim 1, wherein measuring the activity of RPTP-κ comprises measuring the oxidative state of RPTP-κ, wherein a difference in the ratios of oxidized RPTP-κ to total RPTP-κ following UV irradiation in the treated and untreated cells is indicative of the treatment affecting RPTP-κ activity.

3. The method of claim 2, wherein measuring the oxidative state of RPTP-κ comprises immunoblotting using an antibody reactive with an oxidized cysteine residue.

4. The method of claim 2, further comprising identifying the treatment as protecting RPTP-κ activity when the ratio of oxidized RPTP-κ to total RPTP-κ following UV irradiation is less in the treated cell compared to the untreated cell.

5. The method of claim 1, wherein measuring the activity of RPTP-κ comprises measuring phosphatase activity of RPTP-κ, wherein a difference in the phosphatase activities of the treated and untreated cells is indicative of the treatment affecting RPTP-κ activity.

6. The method of claim 5, wherein measuring the phosphatase activity of RPTP-κ comprises using a tyrosine-phosphorylated peptide derived from EGFR.

7. The method of claim 5, further comprising identifying the treatment as protecting RPTP-κ activity when the phosphatase activity is greater in the treated cell compared to the untreated cell.

8. The method of claim 1, wherein the UV radiation is UVA or UVB radiation.

9. The method of claim 1, wherein the cells are cultured cells.

10. The method of claim 1, wherein the method is conducted by high throughput screening using a plurality of cells and plurality of treatments.

\* \* \* \* \*